US006696299B1

(12) United States Patent
Empedocles et al.

(10) Patent No.: US 6,696,299 B1
(45) Date of Patent: Feb. 24, 2004

(54) POLARIZATION LABEL FOR MEASURING 3-DIMENSIONAL ORIENTATION

(75) Inventors: Stephen Empedocles, Palo Alto, CA (US); Moungi Bawendi, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/310,009

(22) Filed: May 11, 1999

(51) Int. Cl.$^7$ ............................................. G01N 37/00
(52) U.S. Cl. ..................... 436/56; 436/172; 436/164; 422/82.05; 422/82.08
(58) Field of Search ............................ 436/56, 8, 164, 436/172, 166; 422/82.05, 82.08, 68.1

(56) References Cited

U.S. PATENT DOCUMENTS 5,786,139 A    7/1998   Burke et al. ................... 435/6

FOREIGN PATENT DOCUMENTS

WO    WO 98 55844    12/1998

OTHER PUBLICATIONS

Bain, et al., "Strong Molecular Alignment in Anisotropic Fluid Media", *Chemical Physics Letters*, 260(3–4): 441–446, 1996.
Chamarro, et al., "Photoluminescence Polarization of Semiconductor Nanocrystals", *Journal of Luminescence*, 70(1–6): 222–237, 1996.
Kuno, et al., "Magnetic Circular Dichroism Study of CdSe Quantum Dots", *Journal of Chemical Physics*, 108(10): 4242–4247, 1998.

Ruiter, et al., "Single Molecule Rotational and Translational Diffusion Observed by Near–Field Scanning Optical Microscopy", *Journal of Physical Chemistry*, 101 (40): 7318–7323,1997.
Smith, et al., "Measurement of Rotational Motion in Membranes Using Fluorescence Recovery After Photobleaching", *Biophysical Journal*, 36(1):73–91, 1981.
Wegener, et al., "Fluorescence Recovery Spectroscopy as a Probe of Slow Rotational Motions", *Biophysical Journal*, 46(6): 795–803, 1984.
Betzig, et al., "Single Molecules Observed by Near–Field Scanning Optical Microscopy," *Science*, 262:1422–1425 (1993).
Bopp, et al., "Single–Molecule Spectroscopy With 27 fs Pulses: Time–Resolved Experiments and Direct Imaging Of Orientational Distributions," *Appl. Phys. Letter*, 73:7–9 (1998).
Bruchez, et al., "Semiconductor Nanocrystals as Fluorescent Biological Labels," *Science*, 262:1422–1425 (1993).
Chan, et al., "Quantum Dot Bioconjugates for Ultrasensitive Nonisotopic Detection," *Science*, 262:1422–1425 (1993).

(List continued on next page.)

*Primary Examiner*—Lyle A. Alexander
(74) *Attorney, Agent, or Firm*—Choate, Hall & Stewart; Valarie B. Rosen

(57) ABSTRACT

A photoactive moiety exhibiting an anisotropic transition dipole. The moiety exhibits emission of polarized light in response to energy absorption. In a preferred embodiment, the moiety comprises a particle from the group consisting of a crystalline arrangement of photoactive molecules and a photoactive nanocrystal. The moiety may include a matrix in which photoactive objects exhibiting an anisotropic emission dipole are embedded. The moiety may be photobleached to product the anisotropy and the photoactive objects may have a one dimensional transition dipole in their natural state.

11 Claims, 2 Drawing Sheets

OTHER PUBLICATIONS

Callomon, et al., "Rotational Analysis of the 2600Å Absorption System of Benzene," *Phil. Trans. R. Soc. Lond. A*, 259:499–532 (1966).

Dabbousi, et al., "(CdSe) ZnS Core–Shell Quantum Dots: Synthesis and Characterization of a Size Series of Highly Luminescent Nancrystallites," *J. Phys. Chem. B*, 101:9463–9475 (1997).

Dickson, et al., "Simultaneous Imaging of Individual Molecules Aligned Both Parallel and Perpendicular to the Optic Axis," *Phys. Rev. Lett*, 81:5322–5325 (1998).

Efros, et al., "Band–edge Exciton In Quantum Dots of Semiconductors With a Degenerate Valence Band: Dark and Bright Exciton States," *Phys. Rev. B.*, 54: 4843–4856 (1996).

Efros, L. "Luminescence Polarization of CdSe Microcrystals," *Phys. Rev. B.*, 46:7448–7458 (1992).

Empedocles, et al., "Three–Dimensional Orientation Measurements of Symmetric Single Chromophores Using Polarization Microscopy," *Nature*, 399:126–130 (1999).

Empedocles, et al., "Photoluminescence Spectroscopy of Single CdSe Nanocrystallite Quantum Dots," *Phys. Rev. Lett.*, 77:3873–3876 (1996).

Empedocles, et al., "Quantum–Confined Stark Effect in Single CdSe Nanocrystallite Quantum Dots," *Science*, 278:2114–2117 (1997).

Fattinger, et al., "Optical–Environment–Dependent Lifetimes and Radiation Patterns to Luminescent Centers in Very Thin Films," *Journal of Luminescence*, 31 & 32:933–935 (1985).

Franceschetti, et al., "Many–body Pseudopotential Theory of Excitons in InP and CdSe Quantum Dots," *Phys. Rev. B.*, 60:1819–1829.

Güttler, et al., "Single Molecule Polarization Spectroscopy: Pentacene in p–Terphenyl," *Chemical Physics*, 211:421–430 (1996).

Ha, et al., "Single Molecule Dynamics Studied by Polarization Modulation," *Phys. Rev. Lett.*, 77:3979–3982.

Hines, et al., "Synthesis and Characterization of Strongly Luminescing ZnS–Capped CdSe Nanocrystals," *J. Phys. Chem.* 100:468–471.

Kneipp, et al., "Single Molecule Detection Using Surface–Enhanced Raman Scattering," (SERS), *Phys. Rev. Lett.*, 78:1667–1670 (1997).

Leung, et al., "Exicton Fine Structure in CdSe Nanoclusters," *Phys. Rev. Lett.*, 57:12291–12301 (1998).

Macklin, et al., "Imaging and Time–Resolved Spectroscopy of Single Molecules at an Interface," *Science*, 272:255–258 (1996).

Murray, et al., "Synthesis and Characterization of Nearly Monodisperse CdE (E × S, Se, Te) Semiconductor Nanocrystallites," *J. Am. Chem. Soc.* 115:8706–8715 (1993).

Sepiol, et al., "Single Molecules Observed by Immersion Mirror Objective. The Orientation or Terrylene Molecules via the Direction of its Transition Dipole Moment," *Chemical Physics Letters*, 273:444–448 (1997).

Shiang, et al., "Symmetry of Annealed Wurtzite CdSe Nanocrystals: Assignment to the $C3_v$ Point Group," *J. Phys. Chem.* 99:17417–17422 (1995).

Tittel, et al., "Investigations of the Emission Properties of Single CDs–Naoncrystallites," *Ber. Bunsenges. Phys. Chem.* 101:1626–1630 (1997).

POLARIZATION LABEL FOR MEASURING 3-DIMENSIONAL ORIENTATION

FIELD OF THE INVENTION

This invention relates to the production and use of polarization labels for identifying three dimensional orientation, more specifically, three dimensional orientation of light emitting and absorbing objects.

BACKGROUND OF THE INVENTION

Fluorescent labeling is a very powerful technique for locating and tracking tagged objects, with applications in areas ranging from molecular dynamics and combinatorial chemistry to security systems and inventory control. However, this technique has several limitations. The number of objects which can be tracked simultaneously is limited by the fluorescent wavelengths available from the tags. In addition, this technique cannot provide information about three dimensional orientation relationships among objects.

A complete description of a three dimensional (3D) system includes analysis of the orientation of its components with respect to each other. For example, the chemical interactions of proteins with each other depend intimately on the spatial relationships they have with each other in all three dimensions. Characterization of an interface requires not only knowledge of the chemistry of the materials at either side of that interface but also of their orientation with respect to the interface and to each other.

Some 3D information about individual molecules or other complexes is available through scanning near-field optical microscopy (SNOM). However, SNOM is a relatively invasive technique which, in addition, can only analyze one small region of a sample at a time. Thus, the technique is not useful for high-throughput screening. Because of the small field of view, only a small total area can be analyzed, resulting in sampling errors. As a result, if a sample exhibits large amounts of variation, SNOM may not reveal the full variability of the sample. While far field microscopy can probe larger areas, it can only provide two-dimensional information about the orientation of a molecule with respect to the plane of the sample under observation.

SUMMARY OF THE INVENTION

In one aspect, the method of determining the orientation of a photoactive moiety exhibiting an anisotropic transition dipole includes exposing the moiety to a light source to stimulate a spectral emission for the moiety and correlating the emission with the orientation of the moiety. The moiety exhibits spectral emission polarized along at most two dimensions. In one embodiment the moiety exhibits emission polarized along two dimensions. The moiety may include a particle from the group consisting of a crystalline arrangement of photoactive molecules and a photoactive nanocrystal. The moiety may include a matrix in which photoactive objects exhibiting an anisotropic emission dipole are embedded. The matrix may be a polymer. In another embodiment, the photoactive objects include a member of the group consisting of a photoactive molecule, a single crystal of photoactive molecules, and a photoactive nanocrystal. The photoactive moiety may further include a magnetic or polar moiety. The photoactive moiety may be photobleached to produce the anisotropy. The transition dipoles of the photoactive objects can be aligned with the photoactive moiety.

In another aspect, a photoactive moiety according to the invention exhibits an anisotropic transition dipole wherein the moiety exhibits emission of polarized light in response to energy absorption. The moiety may include a particle from the group consisting of a crystalline arrangement of photoactive molecules and a photoactive nanocrystal. In one embodiment, the moiety includes a matrix in which photoactive objects exhibiting an anisotropic emission dipole are embedded. In this embodiment, the photoactive objects include a member of the group consisting of a photoactive molecule, a single crystal of photoactive molecules, and a photoactive nanocrystal. The transition dipoles of the photoactive objects may be aligned within the photoactive moiety. The moiety may be photobleached to produce the anisotropy. In one embodiment, the photoactive objects have a one-dimensional transition dipole in their natural state and the moiety emits light polarized in two dimensions. The moiety may emit light polarized in one dimension. In another embodiment, the photoactive objects have a two-dimensional transition dipole in their natural state and the moiety exhibits emission of light polarized in two dimensions.

In yet another aspect, the method of the invention for creating a moiety of photoactive molecules includes entrapping the photoactive molecules in a solid, the photoactive molecules exhibiting an oriented transition dipole, and photobleaching a portion of the photoactive molecules. The moiety will then exhibit polarized light emission in response to light absorption. In one embodiment of this aspect of this invention, the solid is a matrix in which the photoactive molecules are entrapped and the matrix includes a polymer. In this embodiment, the photoactive molecules have a uni-dimensional transition dipole in their natural state. In this invention, the moiety is photobleached with polarized light and after photobleaching the moiety emits light polarized in two dimensions.

In yet another aspect, the method of the invention for providing an identification unit includes selecting an item of interest and providing an identifier wherein the identifier includes at least one particle having characteristic spectral emission. One or more reactive moieties are provided which are attached to the surface of the particle wherein the one or more reactive moieties are selected for their ability to be compatible with the item of interest. The spectral emission of the at least one particle is at least characterized by polarization. In one embodiment, the item of interest is selected from the group consisting of identification tag, security tag, consumer product, fluid, gas, solid, biomolecule, and chemical compound. In another embodiment, the spectral emission of the at least one particle is further characterized by wavelength, intensity, or both.

In yet another aspect, the invention is a library of items of interest wherein each item of interest has associated with it one or more identifiers wherein the one or more identifiers each comprise a particle with a characteristic spectral emission in which the spectral emission is characterized at least in part by polarization. In one embodiment of this aspect of the invention, the item of interest is selected from the group consisting of identification tag, security tag, consumer product, fluid, gas, solid, biomolecule, and chemical compound. The spectral emission of the at least one particle is further characterized by wavelength intensity or both.

Another aspect of the invention is a method of tracking the motion of an item of interest and includes providing an item of interest, wherein the item of interest has associated with it at least one particle having a characteristic spectral emission wherein the spectral emission of the at least one particle is characterized at least in part by polarization. The at least one particle is exposed to an energy source to stimulate the spectral emission and the spectral emission is correlated with the item of interest. These steps are repeated at known intervals.

Still another aspect of the invention is a method of tracking the change in orientation of an item of interest while the item is in motion. The method includes providing an item of interest, wherein the item of interest has associated with it at least one particle having a characteristic spectral emission wherein the spectral emission of at least one particle is characterized at least in part by polarization in two dimensions. The at least one particle is exposed to an energy source to stimulate the spectral emission and the spectral emission is correlated with the orientation of the item of interest. These steps are repeated at known intervals.

In yet another aspect, the invention is method of tracking the change in conformation of an item of interest including providing an item of interest wherein the item of interest has associated with it a plurality of photoactive particles having characteristic spectral emissions and exposing the particles to an energy source to stimulate the spectral emissions. The spectral emissions are correlated with the conformation of the item of interest. Thereafter, these steps are repeated at known intervals. The spectral emissions are characterized at least in part by polarization. In another aspect, the invention describes a method of tracking fluid flow. Identifiers according to the invention are exposed to a light source, such that they will exhibit emission of light in one dimension. The emission is correlated with the position and orientation of at least a portion of the identifiers. The method is repeated to track the change in position (motion). In one embodiment, the motion is tracked sequentially within a series of focal planes. That is, the motion is tracked in one focal plane, and then the focal length adjusted and the motion tracked again.

In another aspect, the invention describes an apparatus for detecting the orientation of a photoactive particle or other item of interest to which the particle might be attached. A detector according to the invention comprises at least three beam splitting mirrors, each of which has a polarizing filter associated with it, and at least one photon detector. The detector also includes means to correlate the spectral emission of the particle to its location and the orientation of its emission, which may include a confocal lensing system, a monochromator, or light filters. The detector may further comprise a second plurality of beam splitting mirrors associated with each polarizing filter and light filters associated therewith.

BRIEF DESCRIPTION OF THE DRAWING

The invention is described with reference to several figures of the drawing, in which.

DETAILED DESCRIPTION

The technology disclosed in this specification allows the measurement of the (3D) orientation of sub-diffraction limited objects. The diffraction limit defines the smallest object which can be viewed using a particular microscopic technique and is approximately half of the wavelength of the electromagnetic radiation being used for the observation. For example, the shortest wavelength of visible light is about 400 nm; therefore, the diffraction limit at this wavelength would be approximately 200 nm. However, while one cannot distinguish the individual features of these objects, one can still determine the location of these sub-diffraction limited objects from the light they emit. With this invention, it is possible to use polarized light to measure the 3D orientation of chromophoric systems with a specific symmetry. It is possible to fabricate fluorescent or absorptive tags with the appropriate symmetry in an arbitrary size range (as small as approximately 10 nm) and from a somewhat arbitrary material, such that the absorption and emission wavelengths can be tuned for a particular application. Indeed, it is not necessary for the fluorescent tag to be a sub-diffraction limited object. Microscopic or even macroscopic objects can also be used and created using the techniques disclosed in this invention. In addition, the excitation need not be optical excitation. The chromophores in the tags may be excited through chemiluminescence, electroluminescence, electrochemiluminescence, thermoluminescence, or cathodoluminescence, or other forms of excitation.

This invention exploits the anisotropic transition dipoles present in many photoactive molecules. In general, transition dipoles in dyes are generally unidirectional. This creates a bright axis which couples to the absorbed or emitted electromagnetic field. Molecules with a more cylindrical symmetry ($C_{3v}$ or higher) may have a degenerate transition dipole oriented isotropically in a plane. These systems are better characterized not by their emission, which is polarized in two dimensions, but by an unique unidirectional dark axis oriented normal to the transition dipole plane, along which no light is emitted. Systems with a potential dark axis include triphenyl methane (Crystal Violet) and its derivative dyes. These molecules are used as biological tags and have also been investigated as individual molecules.

Figure 1:
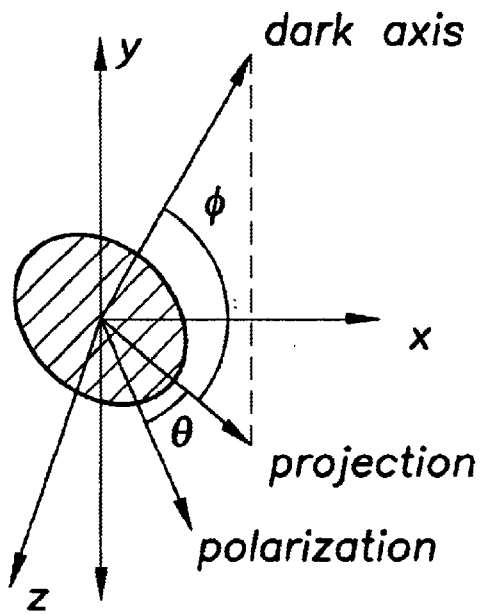
FIG. 1 depicts a general view of a dark axis emitter showing the directions $\Phi$ and $\theta$.
Figure 2A:
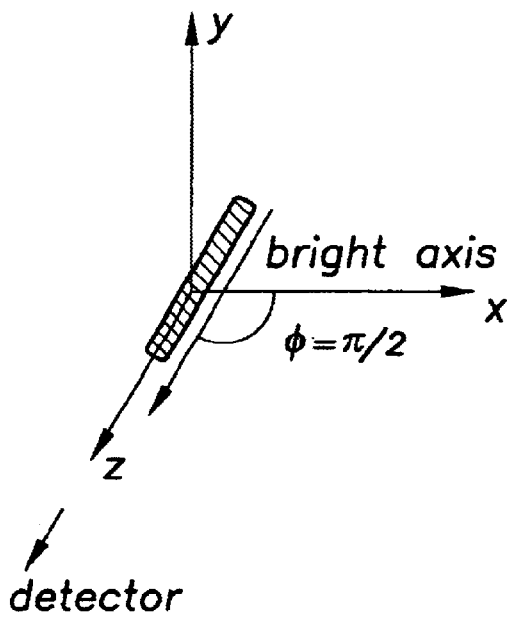
FIGS. 2a–b depict two exemplary orientations of a molecule exhibiting a bright axis with respect to Cartesian axes.
Figure 2B:
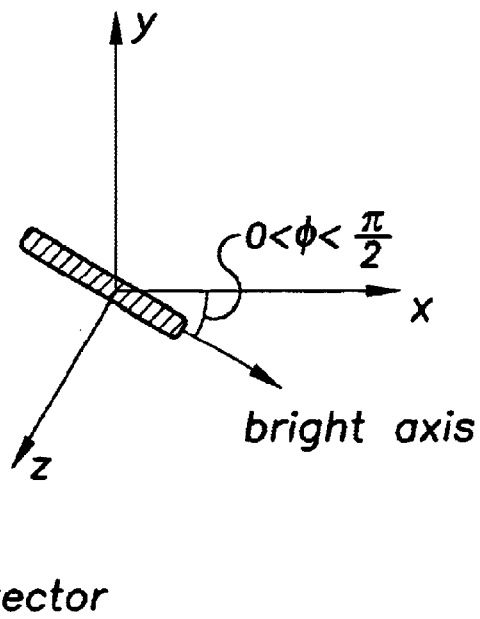
Figure 3A:
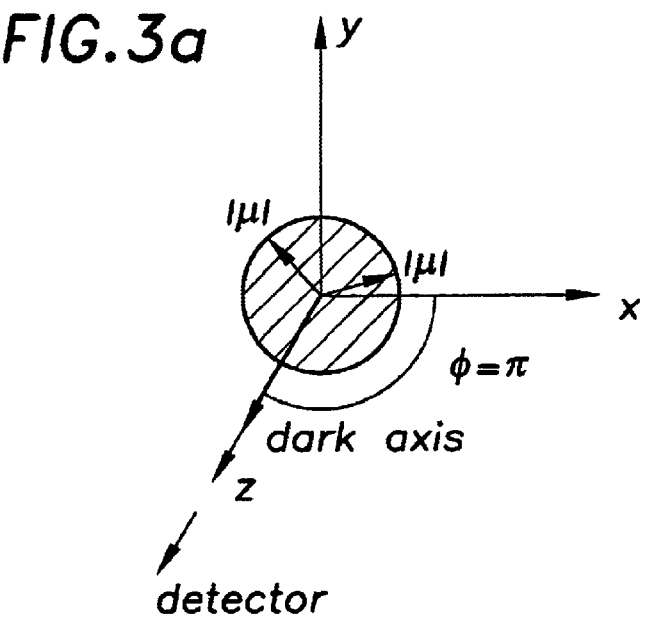
FIGS. 3a–c depict three exemplary orientations of a dark axis emitter, one wherein $\Phi=\pi/2$, one where $0<\Phi<\pi/2$, and one in which $\Phi=0$.
Figure 3B:
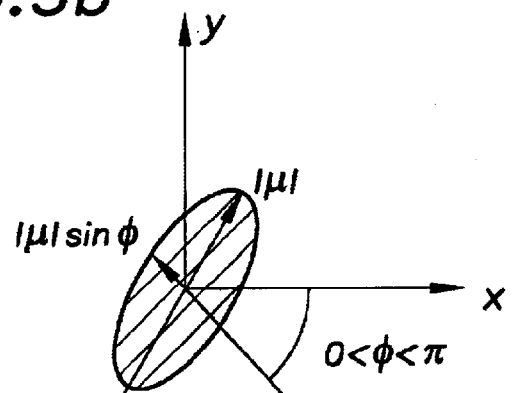
Figure 3C:
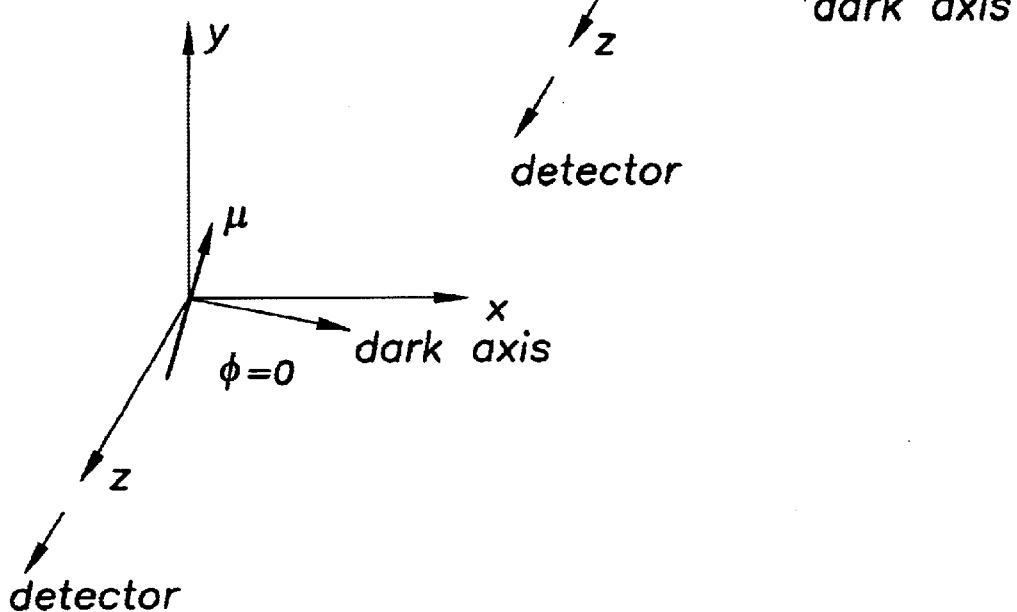

The intensity of an optical transition is proportional to $$|\vec{\mu}\cdot\vec{E}|^2 \tag{1}$$

where $\vec{\mu}$ is the transition dipole vector and $\vec{E}$ is the polarization of the absorbed or emitted light. In systems with a bright axis, the intensity is proportional to $\cos^2(\theta)\cos^2(\Phi)$, where $\theta$ is the angle between the polarization of the light and the projection of $\vec{\mu}$ onto the sample plane, and $\Phi$ is the tilt angle between $\vec{\mu}$ and the sample plane as shown in FIG. 1. Thus, if a polarizer were rotated between the sample and the detector, the intensity of the collected fluorescence would vary between $I_{min}=0$ and $I_{max}=|\vec{\mu}|^2\cdot\cos^2(\Phi)$. In contrast, the intensity of a dark axis transition is proportional to $[1-\cos^2(\theta)\cos^2(\Phi)]$, where $\theta$ and $\Phi$ are now defined with respect to the dark axis and the sample plane. In this case, if a polarizer were rotated between the sample and the detector, the intensity would vary between $I_{max}=|\vec{\mu}|^2$ and $I_{min}=|\vec{\mu}|^2\sin^2(\Phi)$. As a result, the maximum intensity can be measured directly and the value of $\Phi$ calculated from the polarization dependence of the intensity. In more qualitative terms, when the bright axis of a molecule is oriented towards the detector ($\Phi=\pi/2$), no light is emitted in the direction of the detector, as shown in FIG. 2a. However, as shown in FIG. 2b, if the angle $\Phi$ is between 0 and $\pi/2$, then emission can be detected; however, it is difficult to determine experimentally the maximum emission ($\Phi=\pi/2$) because of inhomogeneities in the sample. On the other hand, there is no orientation in which emission cannot be detected from a dark axis emitter. As shown in FIG. 3a, when $\Phi=\pi/2$, the maximum emission intensity is at a maximum, regardless of the polarization of the emitted light. If the dark axis is tilted with respect to the detector, as shown in FIG. 3b, then some polarizations of light will not exhibit maximum intensity $[I_{min}=|\vec{\mu}|^2\sin^2(\Phi)]$. On the other hand, there will always be polarization orientations wherein the emitted light will exhibit maximum intensity ($I_{max}=|\vec{\mu}|^2$). This can be seen even more clearly in FIG. 3c, where $\Phi=0$. The emission is polarized only in one direction, but it exhibits maximum intensity. In conclusion, no matter how the molecule having a dark axis is oriented, the maximum intensity can always be measured for some polarization direction. Therefore, the 3D orientation can be determined.

However, most materials do not intrinsically possess a dark axis. In one embodiment, this invention utilizes photoactive molecules which are entrapped in a polymeric matrix. Many dyes are already commercially available in this form. However, these polymer-dye particles are not useful for this invention in their natural state, even if the constituent molecules possess a bright or dark axis, because the molecules are arranged randomly with respect to each other within the particle. It is possible to fabricate a dark axis emitter from an ensemble of either bright or dark axis chromophores by selectively photobleaching only those chromophores oriented in a given direction. This can be achieved by irradiating the aggregate with high intensity light, causing a permanent chemical change in the chromophores with transition dipoles aligned along the polarization axis of the incident light. Following photobleaching, those chromophores can no longer emit in response to the photobleaching wavelength. If a particle or bead containing bright axis chromophores is photobleached with unpolarized light, the result is a particle which also exhibits a bright axis. It is also possible to create a dark axis particle comprising bright axis molecules by photobleaching with light polarized in one dimension. An aggregate of dark axis molecules which are photobleached with linearly polarized light would still exhibit a dark axis. The particles should be immobilized before photobleaching, otherwise, they will be completely bleached as they rotate. However, if the dye is not particularly robust, and if the photobleaching radiation is very intense and is pulsed very quickly (i.e., nanosecond or microsecond pulses), it is not necessary to immobilize the particles before photobleaching. The total photobleaching time merely needs to be faster than the rotation of the particle.

In another embodiment it is not necessary to photobleach the photoactive molecules which are entrapped in the matrix. Indeed, for this embodiment it is not even necessary to entrap the photoactive molecules inside of a bead. Polarized light can be used to activate one or more transition dipoles in a collection of molecules suspended in a medium. Depending on the pattern of excitation polarization, a artificial, transient bright or dark axis can be created. As these molecules move, they may rotate, rotating the particular transition dipole which was activated. However, at time t=0, all of the activated dipoles were oriented in the same direction. Thus, the rotation of the activated dipoles with time indicates how the orientation changes as the molecules move through the medium. If bright axis chromophores are used, then light polarized in two dimensions should be used to activate them. In this case, two different orientations of transition dipoles are actually activated and there is no emission in the direction from which the absorbed radiation came. If the chromophores are phosphorescent, then motion of these molecules through the medium can be tracked continuously. While the life time of phosphorescence is relatively short, motion can be tracked over long periods of time simply by shining more light into the medium and restimulating the appropriate transition dipoles, as described above.

In another embodiment dark axis emitters are collected in particles which do not then require photobleaching. For example, dye molecules exhibiting a dark axis can be collected in a single crystal, which will then exhibit a dark axis. Alternatively, a nanocrystal or quantum dot can be formulated which exhibits a dark axis. The emission wavelengths of these crystals can be controlled by controlling the size of these crystals as described in our patent application entitled "Inventory Control," U.S. patent application Ser. No. 09/160,458, filed on Sep. 24, 1998, incorporated herein by reference. These nanocrystals can be formulated from semiconductor materials, such as CdSe, and other materials which can be fabricated into nanocrystals. In addition, individual molecules, single crystals, or nanocrystals can be entrapped in a polymeric matrix. If the dye molecules or particles are aligned, for example, with an electric field, before entrapment, then it is not necessary to photobleach the resulting beads or particles.

Individual molecules, quantum dots, single crystals, and beads containing entrapped molecules can all be used to track motion in a gas or liquid. In addition, it is possible to entrap these nanocrystals or single crystals in a polymeric matrix, just as for the individual dye molecules. It is also possible to form a single crystal of nanocrystals.

EXAMPLES

Example 1

In general, fluorescent detection can be used to locate and identify objects. The objects are labeled with identifiers composed of one or more markers which fluoresce at different wavelengths or, perhaps, at different intensities. Depending on the number of different wavelengths and intensities and how the different markers are mixed, a given number of different items can be detected. For example, for a given identifier, one may choose from blue, red, green or orange markers, which in turn may exhibit low or high fluorescent intensity. With this invention, one can add an extra variable, the polarization of the fluorescent emission, thereby increasing the number of different objects which can be detected. The markers would then exhibit a bright or dark axis or isotropic emission. For bright or dark axis molecules, the orientation of the axis can also be used as a label. The markers are irradiated, and the resulting emission correlated with the location of the particle. An appropriate detector, or an array of detectors, may be used to detect individual markers or a large number of markers. If the marker comprises a polymeric particle in which photoactive molecules are entrapped, a magnetic moiety may be added to the marker. The polarization direction of the marker can be varied with respect to the magnetic field orientation of the moiety within the particle. As the markers are irradiated to stimulate emission, they are oriented in an external magnetic field and the direction of emission polarization determined with respect to that magnetic field. A "barcode" comprising one or more photoactive particles produced as described in the Detailed Description, which may vary according to color, type of emission polarization, or direction of emission polarization, may be used to identify or track a particular item of interest.

This technique may be used to identify and follow a wide variety of objects. For example, it could be used to track the progress of a package from a sender, within a delivery organization such as the U.S. Postal Service or commercial package service, to a recipient. It can be used to track manufactured goods as they move through an assembly line or to identify valuables such as jewelry or vehicles. This technique can also be used to tag smaller objects, such as biomolecules. One can also use this technique to identify compounds in combinatorial libraries. For example, as described in our commonly owned patent application U.S. patent application Ser. No. 09/160,458, fluorescent markers can identify individual reaction steps or sets of reactions to track the reagents and solvents used to produce a given molecule within a library. The addition of emission polarization as a variable increases the number of objects, goods, reactions, or other items which can be tracked and identified.

Example 2

This invention can be used according to conventional techniques to identify or track the motion of an object. By repeatedly exciting the markers, the motion of a large number of objects can be detected. The operator can then correlate the emission from the marker with the position of the object being tracked. If the markers are phosphorescent, the motion of the objects can be tracked continuously for short periods of time. Orientation information can be gathered directly if the markers are dark axis emitters. If a magnetic moiety is added to the marker, then the magnetic label can be used to set up an initial orientation with respect to an external magnetic field before the object is set in motion. However, the unique properties of the anisotropic emission dipole enables one to track much more than simple motion from point A to point B. As an object moves, it may change its orientation with respect to a fixed reference axis. As this orientation changes, the marker, which is fixed to the object, will rotate, and this rotation can be recorded as the change in the direction of emission polarization with time. In this case, it is not even necessary to establish absolute orientation; sufficient information can be gathered from the change in orientation with respect to time.

An especially attractive application of this invention is the ability to track the orientation or conformation of a protein or other large, flexible object while it is in motion. This will enable new discoveries in areas such as protein folding and DNA coiling, but has implications for the study of any extensive, flexible item which is allowed to move freely. The item can be tagged at several locations with markers according to the invention. By stimulating emission from the particles at timed intervals, the orientation and position of the various parts of the item can be determined with respect to each other over time. In a preferred embodiment, the marker is a dark axis emitter. Therefore, the absolute orientation of the object can be established at every observation, or the relative or change in orientation can be tracked over time. Again, if a magnetic moiety is included in the marker, then the orientation of the objects can be fixed at an initial position relative to an externally applied magnetic field.

Example 3

This invention can also be used to track the motion of a gas, liquid, or other fluid. In this case, of course, the identifying marker is not attached to the medium. Instead, markers or even free photoactive molecules are simply released within the fluid. Indeed, it is not even necessary to fix the molecules within a matrix so long as they exhibit a bright axis in their natural state. If the medium is irradiated with polarized light, only molecules having the same orientation as the polarization axis of the absorbed radiation will emit light. If the molecules or markers exhibit a bright axis, then the stimulating radiation should be polarized along only two dimensions. Naturally, markers which have been photobleached to produce either a dark or bright axis can also be used to track the motion of the fluid. The radiation absorbed by the markers or molecules creates a transient emission dipole in the collection of markers. That is, because only some of the emission dipoles are stimulated, light is emitted only with polarizations corresponding to those of the absorbed radiation. Thus, the random distribution of dipole orientations within the collection of molecules dispersed in the medium is irrelevant to the observed polarizations of emission. By exciting dipoles oriented in a plane, an artificial oriented transient dipole is created. Confocal microscopy can be used to track the motion of the particles over time. Because confocal microscopy can detect the emission within a single plane without interference from emitters in other planes, it is possible to, plane by plane, build up an image of the motion of the particles through the medium within a given volume. Irradiation of a small volume of material will stimulate emission of a given number of particles which can be tracked by a single microscope or an array of microscopes as they move through the material. The intensity is plotted versus polarization and the data fit to a trigonometric function, from which can be recovered both the in-plane orientation and the tilt of the dipole with respect to the detector. At least three points are necessary to define a curve; the data for these points can be determined by including a series of at least three beam splitters in the detector. If each beam splitter is associated with a polarizing filter oriented at a different angle, the intensities of the various emission polarizations can be measured. The detector can also be set up to detect absorption. In this case, the absorbed or "lost" intensity from the polarization of the incident light is measured.

Other embodiments of the invention will be apparent to those skilled in the art from a consideration of the specification or practice,of the invention disclosed herein. It is intended that the specification and examples be considered as exemplary only, with the true scope and spirit of the invention being indicated by the following claims.

What is claimed is:

1. A photoactive moiety, wherein the moiety axhibits an anisotropic transition dipole characterized by a dark axis, and wherein the moiety has been modified from its natural state to produce the anisotropy.

2. The moiety of claim 1, wherein the moiety comprises a particle from the group consisting of a crystalline arrangement of photoactive molecules and a photoactive nanocrystal.

3. The moiety of claim 1, wherein the moiety comprises a matrix in which photoactive objects exhibiting an anisotropic emission dipole are embedded.

4. The moiety of claim 3, wherein the photoactive objects comprise a member of the group consisting of a photoactive molecule, a single crystal of photoactive molecules, and a photoactive nanocrystal.

5. The moiety of claim 3, wherein the transition dipoles of the photoactive objects are aligned within the photoactive moiety.

6. The moiety of claim 3, wherein the modification comprises photobleaching.

7. The moiety of claim 1, wherein the photoactive objects have a one-dimensional transition dipole in their natural state.

8. The moiety of claim 7, wherein the moiety emits light polarized in two dimensions.

9. The moiety of claim 7, wherein the moiety emits light polarized in one dimension.

10. The moiety of claim 1, wherein the photoactive objects have a two-dimensional transition dipole in their natural state.

11. The moiety of claim 10, wherein the moiety exhibits emission of light polarized in two dimensions.

* * * * *

UNITED STATES PATENT AND TRADEMARK OFFICE
CERTIFICATE OF CORRECTION

PATENT NO. : 6,696,299 B1
DATED : February 24, 2004
INVENTOR(S) : Empedocles et al.

It is certified that error appears in the above-identified patent and that said Letters Patent is hereby corrected as shown below:

<u>Column 1,</u>
Line 7, please insert:
 -- This invention was made with government support under Grant Number DMR-9808941, awarded by The National Science Foundation. The government has certain rights in the invention --.

Signed and Sealed this

Twenty-ninth Day of June, 2004

JON W. DUDAS
*Acting Director of the United States Patent and Trademark Office*